US010054605B2

(12) United States Patent
Shibata et al.

(10) Patent No.: US 10,054,605 B2
(45) Date of Patent: Aug. 21, 2018

(54) SAMPLE ANALYZER

(71) Applicant: Sysmex Corporation, Kobe-shi, Hyogo (JP)

(72) Inventors: Masaharu Shibata, Kobe (JP); Noriyuki Nakanishi, Kakogawa (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 0 days.

(21) Appl. No.: 14/981,047

(22) Filed: Dec. 28, 2015

(65) Prior Publication Data

US 2016/0131674 A1 May 12, 2016

Related U.S. Application Data

(63) Continuation of application No. 13/233,785, filed on Sep. 15, 2011, now Pat. No. 9,250,255, which is a (Continued)

(30) Foreign Application Priority Data

Mar. 18, 2009 (JP) .................................. 2009-065378

(51) Int. Cl.
*G01N 35/10* (2006.01)
*G01N 35/00* (2006.01)

(52) U.S. Cl.
CPC ... *G01N 35/1081* (2013.01); *G01N 35/00603* (2013.01); *G01N 35/00663* (2013.01);
(Continued)

(58) Field of Classification Search
None
See application file for complete search history.

(56) References Cited

U.S. PATENT DOCUMENTS 3,913,577 A 10/1975 Nehra et al.
5,428,993 A 7/1995 Kobashi
(Continued)

FOREIGN PATENT DOCUMENTS

CN 101126762 A 2/2008
CN 101275968 A 10/2008
(Continued)

OTHER PUBLICATIONS

International Search Report dated May 18, 2010 for International Application No. PCT/JP2010/054490, 2 pages.
(Continued)

*Primary Examiner* — Kathryn Wright
(74) *Attorney, Agent, or Firm* — Brinks Gilson & Lione (57) ABSTRACT

A sample analyzer is provided that does not require a plurality of reagent containers containing the same type of reagent to be connected, that can continue measurement even when a reagent container becomes empty, and that allows the timing of replacement of the reagent container to be recognized suitably. A reagent storage section is provided that is connected to a reagent container containing a reagent through a fluid channel and that stores the reagent transferred from the reagent container. A message for prompting replacement of the reagent container is outputted when it is detected that the remaining amount in the reagent container is a predetermined amount or less. A message for prompting to suspend sample measurement in the measurement section is outputted when it is detected that the remaining amount in the reagent storage section is a predetermined amount or less.

5 Claims, 9 Drawing Sheets

Related U.S. Application Data continuation of application No. PCT/JP2010/054490, filed on Mar. 17, 2010.

(52) U.S. Cl.
CPC ....... *G01N 35/00722* (2013.01); *G01N 35/10* (2013.01); *G01N 35/1002* (2013.01); *G01N 2035/00217* (2013.01); *G01N 2035/00673* (2013.01); *G01N 2035/1051* (2013.01)

(56) References Cited

U.S. PATENT DOCUMENTS

| | | |
|---|---|---|
| 5,800,056 A | 9/1998 | Suzuki et al. |
| 6,267,927 B1 | 7/2001 | Pomar Longedo et al. |
| 6,691,748 B1 | 2/2004 | Tajima |
| 7,171,863 B2 | 2/2007 | Tamura et al. |
| 8,082,113 B2 | 12/2011 | Nagai et al. |
| 2002/0031837 A1 | 3/2002 | Matsubara et al. |
| 2002/0051737 A1 | 5/2002 | Sollböhmer et al. |
| 2005/0013744 A1 | 1/2005 | Nagai et al. |
| 2007/0086923 A1 | 4/2007 | Li et al. |
| 2008/0063570 A1 | 3/2008 | Fujino et al. |
| 2010/0104478 A1 | 4/2010 | Kondou |
| 2010/0161243 A1 | 6/2010 | Nagai et al. |

FOREIGN PATENT DOCUMENTS

| | | |
|---|---|---|
| JP | 58-105065 A | 6/1983 |
| JP | 05-084864 U | 11/1993 |
| JP | 06-003364 A | 1/1994 |
| JP | 2531074 Y2 | 4/1997 |
| JP | 10-002902 A | 1/1998 |
| JP | 11-248714 A | 9/1999 |
| JP | 11-300105 A | 11/1999 |
| JP | 2003-066049 A | 3/2003 |
| JP | 2005-305396 A | 11/2005 |
| JP | 2006-003181 A | 1/2006 |
| JP | 2008-249659 A | 10/2008 |
| WO | WO 2007/047069 A2 | 4/2007 |
| WO | WO 2009/031461 A1 | 3/2009 |
| WO | WO 2010/107042 A1 | 9/2010 |

OTHER PUBLICATIONS

Search Report dated Jun. 24, 2013 for corresponding Chinese Patent Application No. 2010800124574, 20 pages.

SAMPLE ANALYZER

RELATED APPLICATIONS

This application is a continuation of U.S. application Ser. No. 13/233,785 filed on Sep. 15, 2011, which is a continuation of PCT/JP2010/054490 filed on Mar. 17, 2010, which claims priority to Japanese Application No. 2009-065378 filed on Mar. 18, 2009. The entire contents of these applications are incorporated herein by reference.

BACKGROUND OF THE INVENTION

1. Field of the Invention

The present invention relates to sample analyzers for analyzing samples using reagents.

2. Description of the Related Art

Conventionally, a number of sample analyzers have been developed that analyze samples such as blood, blood serum, blood plasma, urine, or spinal fluid using reagents. In such sample analyzers, when reagent containers containing reagents to be used for sample measurement become empty, samples cannot be measured during replacement of the empty reagent containers.

WO2007/047069 discloses a system in which even when a reagent container containing a reagent becomes empty, the reagent can be processed continuously. The system disclosed in WO2007/047069 includes a feeder chamber and a buffer chamber between the reagent container and a reagent consuming station. Therefore, even if the reagent container becomes empty, the reagent remaining in the feeder chamber and the buffer chamber can be processed continuously.

Furthermore, U.S. Pat. No. 5,428,993 also discloses an automatic analyzer in which even when a reagent container containing a reagent becomes empty, sample measurement can be continued. In the automatic analyzer disclosed in U.S. Pat. No. 5,428,993, a main reagent container and a sub reagent container are connected to each other through a valve. When the main reagent container becomes empty, the valve is switched to the sub reagent container side. This allows sample measurement to be continued using the reagent contained in the sub reagent container.

Moreover, the automatic analyzer of U.S. Pat. No. 5,428,993 outputs a warning when the total amount of the reagent remaining in the main reagent container and the reagent remaining in the sub reagent container becomes less than a predetermined amount. Furthermore, the automatic analyzer outputs a warning message indicating a shortage of the reagent when one of the reagent containers becomes empty.

WO2007/047069 neither discloses nor suggests any operation that the system disclosed therein carries out when the reagent container becomes empty. The user of the system, therefore, was not able to determine the timing of replacement of the reagent container. On the other hand, the automatic analyzer disclosed in U.S. Pat. No. 5,428,993 outputs the warning message indicating the shortage of the reagent when one of the reagent containers becomes empty. Thus, the user of the automatic analyzer can recognize the shortage of the reagent.

However, the automatic analyzer disclosed in U.S. Pat. No. 5,428,993 is based on the premise that a plurality of reagent containers containing the same type of reagent are connected. Therefore, the automatic analyzer is different in the premise from the system of WO2007/047069 that is not based on the premise that a plurality of reagent containers containing the same type of reagent are connected.

SUMMARY OF THE INVENTION

The scope of the present invention is defined solely by the appended claims, and is not affected to any degree by the statements within this summary.

A first sample analyzer embodying features of this invention comprises: a reagent storage section that is connected to a reagent container containing a reagent through a fluid channel and that stores the reagent transferred from the reagent container; a measurement section that is connected to the reagent storage section through a fluid channel and that measures a sample using the reagent; a transfer unit that transfers the reagent from the reagent container to the reagent storage section and then from the reagent storage section to the measurement section; a reagent container remaining amount detection means for detecting that the remaining amount in the reagent container is a predetermined amount or less; and a replacement message output means that outputs a message for prompting replacement of the reagent container when the reagent container remaining amount detection means detects that the remaining amount in the reagent container is the predetermined amount or less.

A second sample analyzer embodying features of this invention comprises: a sample analyzer, comprising: a reagent storage chamber that is connected to a reagent container containing a reagent through a fluid channel and that stores the reagent transferred from the reagent container; a measurement section that is connected to the reagent storage chamber through a fluid channel and that measures a sample using the reagent; a transfer unit that transfers the reagent from the reagent container to the reagent storage section and then from the reagent storage section to the measurement section; a reagent container remaining amount detection section that detects the remaining amount in the reagent container; an output device that outputs a predetermined information; and a controller that controls operation of the reagent storage chamber, the measurement section, the transfer unit, the reagent container remaining amount detection section, and the output device, wherein the controller controls the output device to output a message for prompting replacement of the reagent container when the remaining amount in the reagent container detected by the reagent container remaining amount detection section is a predetermined amount or less.

DETAILED DESCRIPTION OF THE PREFERRED EMBODIMENTS

Embodiment 1

Figure 1:
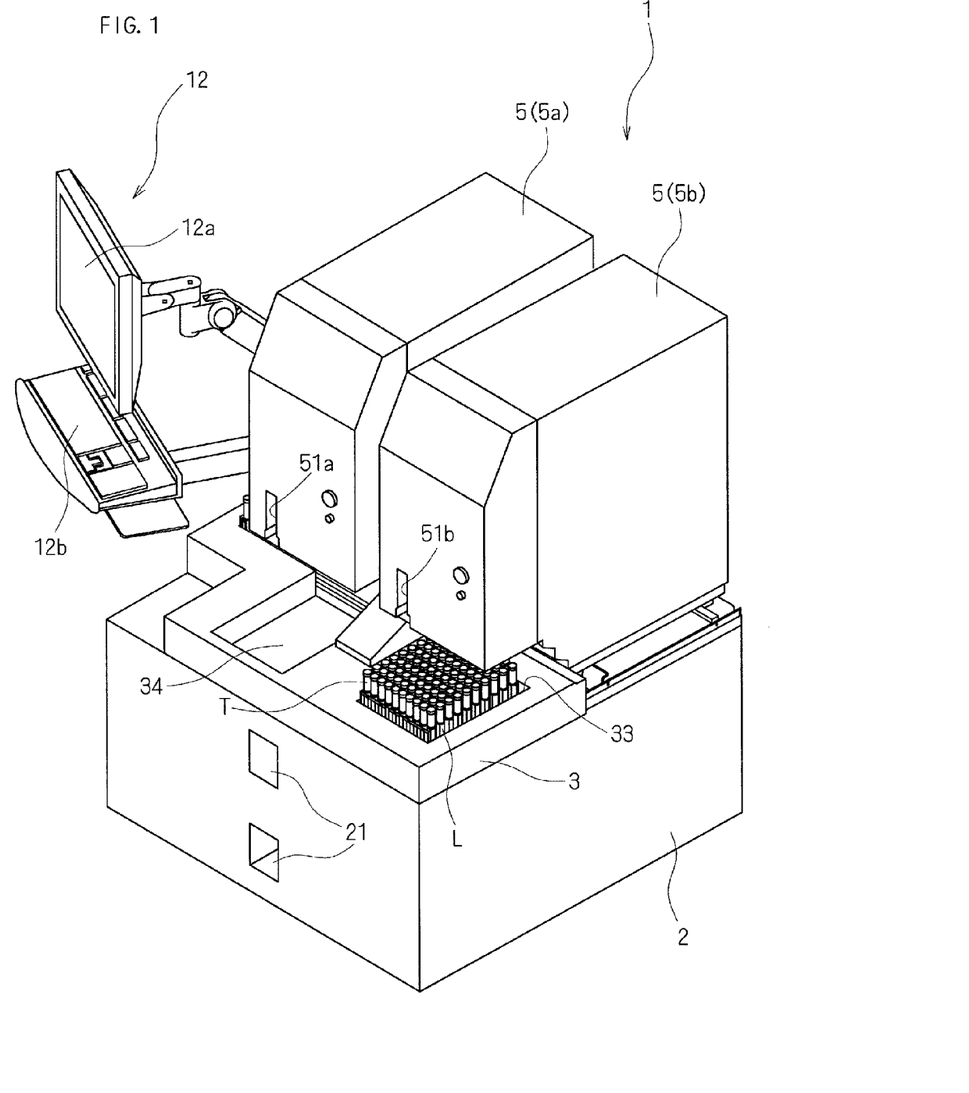
FIG. 1 is a schematic view showing the outline configuration of a sample analyzer according to Embodiment 1 of the present invention.

FIG. 1 is a schematic view showing the outline configuration of a sample analyzer according to Embodiment 1 of the present invention. The sample analyzer 1 according to Embodiment 1 of the present invention comprises two measurement units (measurement section) 5a, 5b of the same type, a sample transporting unit 3 arranged on the front side of the measurement units 5a, 5b, and a control unit 12, which is configured with a personal computer (PC) electrically connected to the measurement units 5a, 5b and the sample transporting unit 3.

In Embodiment 1, the measurement units 5a and 5b are the same type of measurement units and measure samples with respect to the same measurement item using the same measurement principle. In this connection, the term "same type" includes not only the case where the two measurement units 5a, 5b measure samples with respect to exactly the same measurement item but also the case where a plurality of measurement items with respect to which the measurement unit 5a measures samples are partly common with a plurality of measurement items with respect to which the measurement unit 5b measures samples. Hereinafter, Embodiment 1 is described using an example in which the measurement units 5a, 5b are blood cell counters. However, the type of the measurement units 5a, 5b is not limited thereto and they can obviously be, for example, urine analyzers, blood coagulation measurement apparatuses, immunology analyzers, or gene amplification measurement apparatuses.

Furthermore, the measurement units 5a, 5b are arranged in parallel. Moreover, the measurement units 5a, 5b each take a sample container T, which is held by a sample rack L that the sample transporting unit 3 transports, thereinto through a corresponding loading port 51a, 51b provided for the housing thereof and then measure the sample aspirated by an internal aspiration section (not shown in the drawings) with respect to a predetermined measurement item.

A reagent container setting section 2 in which an air pressure source unit and a reagent container can be set is provided in the lower part of the sample analyzer 1 according to Embodiment 1. Furthermore, a reagent storage section that stores the reagent transferred from the reagent container by operation of the air pressure source unit is provided inside the reagent container setting section 2. Accordingly, the reagent storage section is ensured without an increase in setting space. The reagent is replenished by bringing out the reagent container through the reagent-replacement openings 21, 21 to replace it as a whole.

Figure 2:
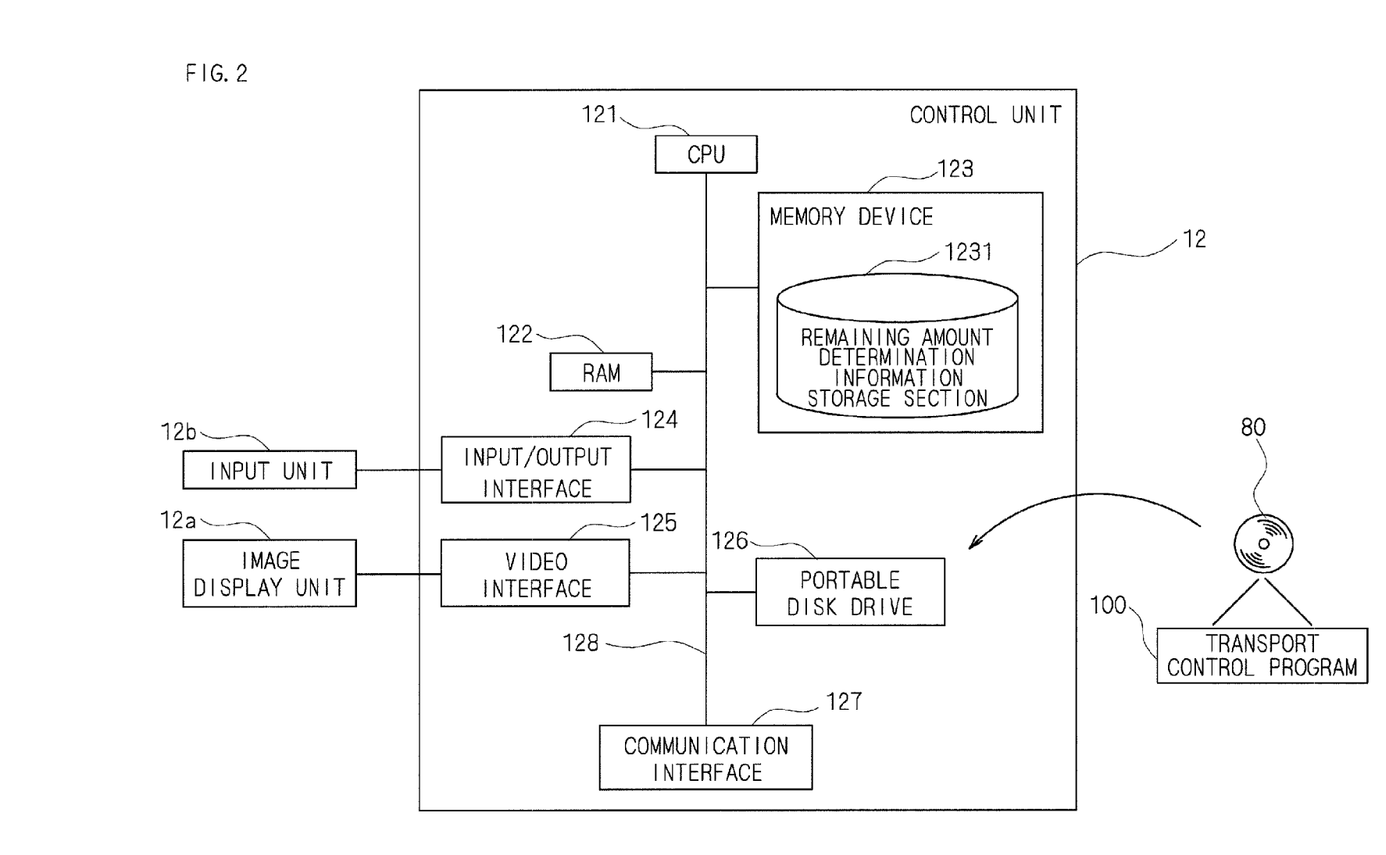
FIG. 2 is a block diagram showing the configuration of a control unit of the sample analyzer according to Embodiment 1 of the present invention.

The control unit 12 is configured with, for example, a personal computer (PC). FIG. 2 is a block diagram showing the configuration of the control unit 12 of the sample analyzer 1 according to Embodiment 1 of the present invention. As shown in FIG. 2, the control unit 12 is composed of a CPU (control section) 121, a RAM 122, a memory device 123, an input/output interface 124, a video interface 125, a portable disk drive 126, a communication interface 127, and an internal bus 128 that connects the above-mentioned hardware.

The CPU (control section) 121 is connected to each of the above-mentioned hardware of the control unit 12 through the internal bus 128. The CPU 121 serves as a control section that controls operation of each of the above-mentioned hardware and also executes various software functions according to a transport control program 100 stored in the memory device 123. The RAM 122 is configured with a volatile memory such as a SRAM or a SDRAM. The RAM 122 expands a load module when the transport control program 100 is executed, and stores, for example, temporary data generated during the execution of the transport control program 100.

The memory device 123 is configured with, for example, an internal fixed storage device (hard disk) or a ROM. The transport control program 100 stored in the memory device 123 is downloaded by the portable disk drive 126 from a portable recording medium 80 such as a DVD or a CD-ROM in which information such as a program and data is stored, and is expanded from the memory device 123 to the RAM 122 to be executed. Obviously, it may also be a computer program downloaded from an external computer connected to the network through the communication interface 127. Furthermore, the memory device 123 is provided with a remaining amount determination information storage section 1231 that stores the remaining amount determination information for determining the remaining amount in the reagent container or the reagent storage section. The remaining amount determination information storage section 1231 stores, for example, a reagent container remaining amount to serve as a criterion for determining that the reagent container becomes empty and a reagent storage remaining amount to serve as a criterion for determining that the reagent storage section becomes empty.

The communication interface 127 is connected to the internal bus 128 and is connected to an external network such as the Internet, LAN, or WAN, which makes it possible to transmit data to or receive data from, for example, an external computer.

The input/output interface 124 is connected to an input unit 12b such as a keyboard or a mouse and accepts data inputs. Furthermore, the video interface 125 is connected to an image display unit 12a such as a CRT monitor or an LCD and displays predetermined images.

Figure 3:
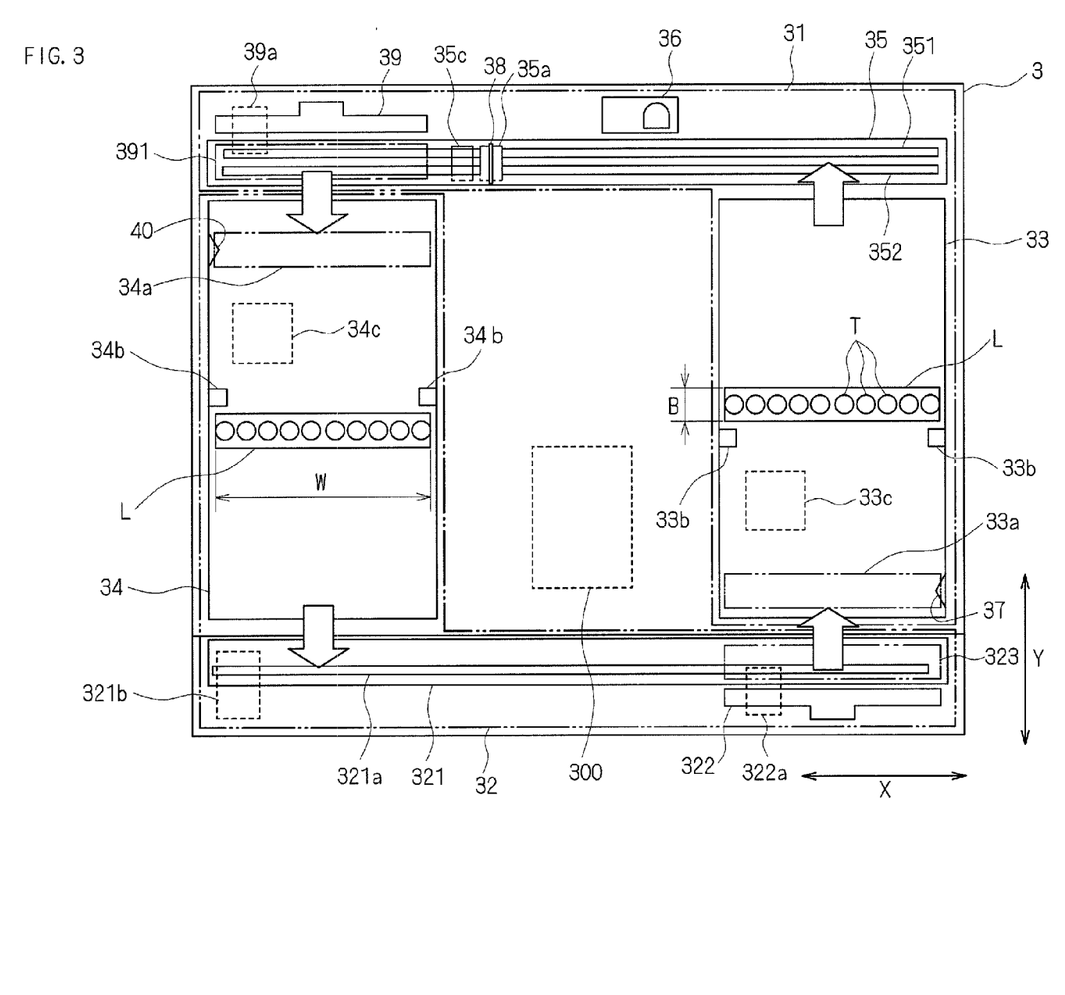
FIG. 3 is a schematic view showing the outline configuration of a sample transporting unit of the sample analyzer according to Embodiment 1 of the present invention.

FIG. 3 is a schematic view showing the outline configuration of the sample transporting unit 3 of the sample analyzer 1 according to Embodiment 1 of the present invention. As shown in FIG. 3, the sample transporting unit 3 comprises a first transport mechanism 31 for supplying samples to the measurement unit 5a or 5b of the sample analyzer 1, a second transport mechanism 32 for transporting the samples to the sample transporting unit 3 located on the downstream side, and a control section 300 for controlling the second transport mechanism 32. The first transport mechanism 31 comprises a pre-analysis rack holder 33 that can temporarily hold a plurality of sample racks L, each of which holds a plurality of sample containers T containing samples to be analyzed, a rack transport unit 35 that linearly moves the sample racks L horizontally in the direction shown with the arrow X in FIG. 3, a bar code reader 36 that reads bar codes of bar code labels attached to the sample containers T and bar codes of bar code labels attached to the sample racks L, a rack sensor 37 that detects the presence or absence of the sample racks L, a sample container sensor 38 that detects the presence or absence of the sample containers T, and a rack feeding unit 39 that feeds the sample racks L to a post-analysis rack holder 34.

The pre-analysis rack holder 33 has a rectangular shape in a planar view and has a width in the X-direction that is slightly wider than the width in the X-direction of the sample rack L. The pre-analysis rack holder 33 is formed to have an upper surface that is one level lower than the plane surrounding it, and the pre-analysis sample rack L is placed on the upper surface thereof. The pre-analysis rack holder 33 works with the second transport mechanism 32. A rack feeding unit 322 of the second transport mechanism 32 described later feeds the sample rack L from the second transport mechanism 32.

The rack sensor 37 is attached in the vicinity of the pre-analysis rack holder 33, and the position where the rack sensor 37 detects the presence or absence of the sample rack L is a rack detection position 33a. The sample rack L fed from the second transport mechanism 32 is transported up to the rack detection position 33a and then the sample rack L thus transported is detected by the rack sensor 37.

Furthermore, both side surfaces of the pre-analysis rack holder 33 are provided with rack feed-in parts 33b, 33b, respectively, that can project inwardly. When the rack sensor 37 detects the sample rack L, the rack feed-in parts 33b, 33b project to engage with the sample rack L and move backwards (in the direction approaching the rack transport unit 35) in the engaged state and thereby the sample rack L is transferred backwards. The rack feed-in parts 33b, 33b are driven by a stepping motor 33c provided in the lower part of the pre-analysis rack holder 33.

The rack transport unit 35 transports the sample rack L, which has been transferred by the pre-analysis rack holder 33, in the X-direction. A sample container detecting position 35a where the sample container sensor 38 detects the presence or absence of the sample container T and a sample supply position 35c where the sample is supplied to the measurement unit 5 exist on the route on which the rack transport unit 35 transports the sample rack L. The rack transport unit 35 transports the sample rack L to the sample supply position 35c through the sample container detecting position 35a.

The sample supply position 35c is located downstream in the transporting direction by the distance equal to the width of one sample container T from the sample container detecting position 35a. When the sample rack L is transported to the sample supply position 35c by the rack transport unit 35, hands not shown in the drawings of the measurement unit 5 hold the sample container T held by the sample rack L and remove the sample container T from the sample rack L. The sample is aspirated from the sample container T to be supplied to the measurement unit 5. After transporting the sample container T to the sample supply position 35c, the rack transport unit 35 suspends transportation of the sample rack L until the sample container T is returned to the sample rack L after completion of supply of the sample.

Furthermore, the rack transport unit 35 includes two annular belts, specifically a first belt 351 and a second belt 352 that are movable independently from each other. The width of each of the first belt 351 and the second belt 352 in the arrow Y direction is not wider than half the width B of the sample rack L in the arrow Y direction. The first belt 351 and the second belt 352 are arranged in parallel in such a manner as not to protrude from the width B of the sample rack L in the arrow Y direction when the rack transport unit 35 transports the sample rack L. The direction in which the first belt 351 and the second belt 352 move is controlled and thereby the sample rack L can be moved linearly not only in the forward direction but also in the reverse direction in the X-direction.

The bar code reader 36 reads the bar code of the bar code label attached to the sample container T and the bar code of the bar code label attached to the sample rack L. The bar code reader 36 reads the sample bar code of the sample container T while a rotation device not shown in the drawings rotates a target sample container T horizontally, with the target sample container T being held by the sample rack L. The rotation of the sample container T allows the bar code label to face toward the bar code reader 36 even when the bar code label of the sample container T is on the opposite side of the bar code reader 36. Thus, the bar code reader 36 is allowed to read the sample bar code of the sample container T. The rack bar code of the sample rack L has a record of a rack ID uniquely provided for each sample rack L and is used in, for example, managing the result of sample analysis.

The rack sensor 37 and the sample container sensor 38 each are a contact sensor and include a curtain-shaped contact segment not shown in the drawings, a light emitting element that emits light, and a light receiving element. In each of the rack sensor 37 and the sample container sensor 38, the contact segment comes into contact with an object to be detected and thereby is bent. As a result, light emitted from the light emitting element is reflected by the contact segment to enter the light receiving element. Thus, when the sample container T to be detected that is held by the sample rack L passes directly under the sample container sensor 38, the contact segment comes into contact with the sample container T to be bent and thereby the sample container T can be detected.

The rack feeding unit 39 is arranged to the rearward of the post-analysis rack holder 34 in such a manner as to face the post-analysis rack holder 34, with the rack transport unit 35 being interposed therebetween. The rack feeding unit 39 linearly moves horizontally to the arrow Y direction with the driving force provided by the stepping motor 39a. Thus, when the sample rack L is transported to a position 391 between the post-analysis rack holder 34 and the rack feeding unit 39, the rack feeding unit 39 is moved towards the post-analysis rack holder 34 to push and move the sample rack L, which allows the sample rack L to be transported into the post-analysis rack holder 34. In this manner, the sample rack L holding the sample container of the sample whose analysis is completed is fed from the first transport mechanism 31 to the second transport mechanism 32.

As shown in FIG. 3, the second transport mechanism 32 comprises a rack transport unit 321, the rack feeding unit 322, and the post-analysis rack holder 34. The rack transport unit 321 extends in the X-direction and can linearly move the sample rack L horizontally in the X-direction. The rack transport unit 321 includes an annular belt 321a and a stepping motor 321b and moves the belt 321a in the X-direction with the driving force provided by the stepping motor 321b. Thus, the sample rack L placed on the belt 321a can be transported in the X-direction.

The rack feeding unit 322 is arranged in front of the pre-analysis rack holder 33 in such a manner as to face the pre-analysis rack holder 33, with the rack transport unit 321 being interposed therebetween. The rack feeding unit 322 linearly moves horizontally to the arrow Y direction with the driving force provided by a stepping motor 322a. Thus, when the sample rack L is transported to a position 323 between the pre-analysis rack holder 33 and the rack feeding unit 322, the rack feeding unit 322 is moved towards the pre-analysis rack holder 33 to push and move the sample rack L, which allows the sample rack L to be transported to the rack detection position 33a inside the pre-analysis rack holder 33.

The post-analysis rack holder 34 has a rectangular shape in a planar view and has a width in the X-direction that is slightly wider than the width in the X-direction of the sample rack L. The post-analysis rack holder 34 is formed to have an upper surface that is one level lower than the plane surrounding it, and the sample rack L holding the sample container of the sample whose analysis is completed is placed on the upper surface thereof. The post-analysis rack holder 34 works with the first transport mechanism 31. The rack feeding unit 39 feeds the sample rack L from the first transport mechanism 31.

Both side surfaces of the post-analysis rack holder 34 are provided with rack feed-in parts 34b, 34b, respectively, that can project inwardly. The sample rack L fed from the first transport mechanism 31 by the rack feeding unit 39 is transported to the rack detection position 34a. When the sample rack L thus transported is detected by a rack sensor 40, the rack feed-in parts 34b, 34b project to engage with the sample rack L and move forwards (in the direction approaching the rack transport unit 321) in the engaged state and thereby the sample rack L is transferred forwards. The rack feed-in parts 34b, 34b are driven by a stepping motor 34c provided in the lower part of the post-analysis rack holder 34.

Transportation of the sample rack L by the sample transporting unit 3 is controlled by the control unit 12 that is connected to the sample transporting unit 3 in such a manner as to be capable of data communication therewith. The sample transporting unit 3 comprises the control section 300 configured with, for example, a CPU, a ROM, or a RAM. The control unit 12 can control operation of the sample transporting unit 3 through data communication with the control section 300.

Figure 4:
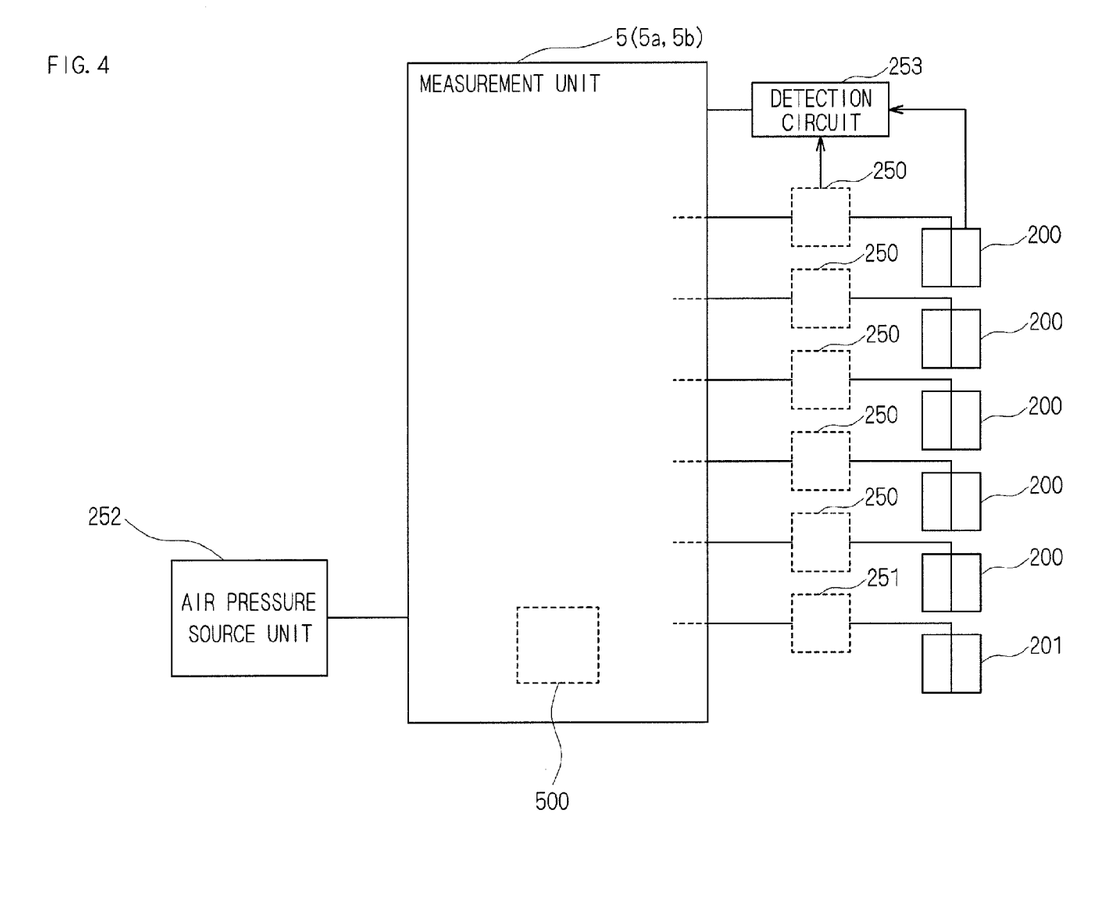
FIG. 4 is a block diagram showing the configuration of a reagent remaining amount detection means of the sample analyzer according to Embodiment 1 of the present invention.

FIG. 4 is a block diagram showing the configuration of a reagent remaining amount detection means (a reagent container remaining amount detection section or a storage remaining amount detection section) of the sample analyzer 1 according to Embodiment 1 of the present invention. As shown in FIG. 4, reagents are supplied to the measurement unit 5 (5a, 5b) from reagent containers 200, 200, . . . and a reagent container 201. In Embodiment 1, reagent storage sections 250, 250, . . . and a reagent storage section 251 that store the reagents are provided between the measurement unit 5 (5a, 5b) and the reagent containers 200, 200, . . . and the reagent container 201. The reagent container 201 contains a reagent that is also used as a diluent, a lavage fluid, and a sheath fluid, and the amount of the reagent contained therein is larger than those contained in the other reagent containers 200, 200, . . . . Therefore, the amount of the reagent stored in the reagent storage section 251 also is larger than those stored in the other reagent storage sections 250, 250, . . . .

An air pressure source unit (transfer unit) 252 has a function of transferring reagents to the measurement unit 5 (5a, 5b) or transferring reagents from the reagent containers 200, 200, . . . and the reagent container 201 by providing positive pressure or negative pressure for the reagent storage sections 250, 250, . . . and the reagent storage section 251.

A detection circuit 253 detects that the remaining amount in each of the reagent containers 200, 200, . . . and the reagent container 201 and/or the reagent storage sections 250, 250, . . . and the reagent storage section 251 is a predetermined amount or less. With respect to the detection method, the method for detecting the remaining amount of the reagent contained in each of the reagent containers 200, 200, . . . and the reagent container 201 is different from the method for detecting the remaining amount of the reagent stored in each of the reagent storage sections 250, 250, . . . and the reagent storage section 251.

For example, when float switches described later are used as the remaining amount detection method for detecting that the remaining amount in each of the reagent containers 200, 200, . . . and the reagent container 201 is a predetermined amount or less, the detection circuit 253 receives signals from the float switches and transmits predetermined signals to the measurement unit 5 (5a, 5b).

The measurement unit 5 (5a, 5b) contains a control section 500 configured with, for example, a processor and a memory and is connected to the CPU 121 of the control unit 12 and the control section 300 of the sample transporting unit 3 in such a manner as to be capable of data communication therewith. The control section 500 controls operation of the measurement unit 5 (5a, 5b) and the transportation of reagents in the reagent container setting section 2. That is, the control section 300 and the control section 500 control operation of the measurement unit 5 (5a, 5b) and the transportation of reagents in the reagent container setting section 2 in response to commands from the CPU 121 of the control unit 12.

Figure 5:
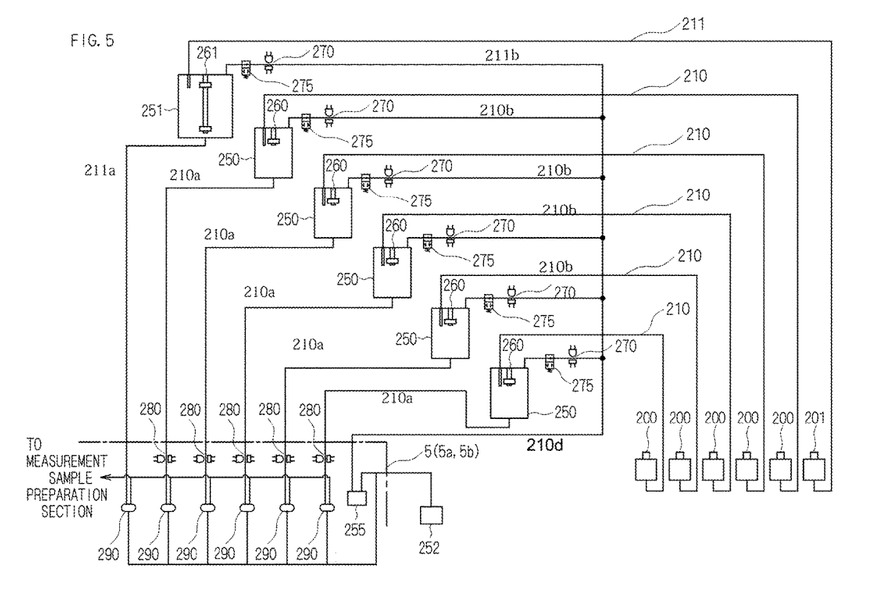
FIG. 5 is a circuit diagram showing the configuration of a reagent supply circuit of the sample analyzer according to Embodiment 1 of the present invention.

FIG. 5 is a circuit diagram showing the configuration of a reagent supply circuit of the sample analyzer 1 according to Embodiment 1 of the present invention. In the example shown in FIG. 5, float switches 260, 260, . . . and a float switch 261 are used as the reagent remaining amount detection means. In FIG. 5, reagents are supplied to the measurement unit 5 (5a, 5b) from the reagent containers 200, 200, . . . and the reagent container 201 through fluid channels 210, 210, . . . and a fluid channel 211. Chambers are arranged as the reagent storage sections 250, 250, . . . and the reagent storage section 251 midway through the fluid channels 210, 210, . . . and the fluid channel 211, respectively.

During the start-up of the sample analyzer 1 or replacement of the reagent containers 200, 200, . . . and the reagent container 201, negative pressure is applied by the air pressure source unit 252 to fluid channels 210d (see FIG. 5) (i.e., also known as third fluid channels) which are connected to the air pressure source unit 252 via a waste fluid chamber 255 for containing waste fluid, to open valves 275, 275, . . . and thereby reagents are transferred from the reagent containers 200, 200, . . . and the reagent container 201 to the reagent storage sections 250, 250, . . . and the reagent storage section 251. Then, the reagent storage sections 250, 250, . . . and the reagent storage section 251 as well as the fluid channels (i.e., also known as first fluid channels) 210, 210, . . . and the fluid channel (i.e., first fluid channel) 211 are filled with the reagents and thereby air bubbles are removed. Whether the reagent storage sections 250, 250, . . . and the reagent storage section 251 as well as the fluid channels 210, 210, . . . and the fluid channel 211 (i.e., first fluid channel) have been filled with the reagents is determined by whether the air bubble sensors 270, 270, . . . detect air bubbles.

When diaphragm pumps 290, 290, . . . are driven by the air pressure source unit 252, with the reagent storage sections 250, 250, . . . and the reagent storage section 251 as well as the fluid channels (i.e., also known as first fluid channels) 210, 210, . . . and the fluid channel (i.e., first fluid channel) 211 being filled with the reagents, the reagents are transferred from the reagent storage sections 250, 250, . . . and the reagent storage section 251 to the measurement unit 5 (5a, 5b) through fluid channels (i.e., also known as second fluid channels) 210a and 211a, respectively. The diaphragm pumps 290, 290, . . . measure the amount of the reagents transferred to the measurement unit 5 (5a, 5b) and then the reagents are transferred to the measurement sample preparation section to be mixed with samples. Thus, measurement samples are prepared. Even when the reagent containers 200, 200, . . . and the reagent container 201 are replaced, reagents are transferred continuously from the reagent storage sections 250, 250, . . . and the reagent storage section 251 to the measurement unit 5 (5a, 5b), that is, the samples are measured continuously by the measurement unit 5 (5a, 5b).

The float switches 260, 260, . . . and the float switch 261 are provided inside the reagent storage sections 250, 250, . . . and the reagent storage section 251. Each float switch 260 or the float switch 261 outputs an ON signal or an Off signal depending on whether a specific amount of reagent is stored inside each reagent storage section 250 or the reagent storage section 251. When the reagents are transferred from the reagent storage sections 250, 250, . . . and the reagent storage section 251 to the measurement unit 5 (5a, 5b) and thereby float boards of the float switches 260, 260, . . . and the float switch 261 descend, as in the case during the start-up of the sample analyzer 1 or replacement of the reagent containers 200, 200, . . . and the reagent container 201, negative pressure is applied by the air pressure source unit 252 to fluid channels 210d (see FIG. 5) (i.e., also known as third fluid channels) which are connected to the air pressure source unit 252 via the waste fluid chamber 255, to open the valves 275, 275, . . . and thereby reagents are transferred to fluid channels (i.e., also known as first fluid channels) 210 and 211 (see FIG. 5), respectively from the reagent containers 200, 200, . . . and the reagent container 201 to the reagent storage sections 250, 250, . . . and the reagent storage section 251. Transfer of the reagents is suspended at the time when the float boards of the float switches 260, 260, . . . and the float switch 261 each return to the position (upper end position) at which they were located before descending.

On the other hand, in the case where the reagents are transferred from the reagent containers 200, 200, . . . and the reagent container 201 to the reagent storage sections 250, 250, . . . and the reagent storage section 251, even when a specific period of time has passed after negative pressure was applied by the air pressure source unit 252, if the float boards of the float switches 260, 260, . . . and the float switch 261 do not return to the upper end position, it can be detected that the remaining amount in each of the reagent containers 200, 200, . . . and the reagent container 201 is a predetermined amount or less and thereby a message (a replacement message) for prompting replacement of reagent containers, such as "Please replace the reagent container" or "No reagent", is outputted to the image display unit 12a of the control unit 12. That is, when a sufficient amount of reagent does not remain in each of the reagent containers 200, 200, . . . and the reagent container 201, the reagents cannot be transferred to the reagent storage sections 250, 250, . . . and the reagent storage section 251 and thereby the float boards of the float switches 260, 260, . . . and the float switch 261 that have descended do not ascend, that is, the remaining amount in each of the reagent storage sections 250, 250, . . . and the reagent storage section 251 does not increase. Accordingly, depending on whether the float boards of the float switches 260, 260, . . . and the float switch 261 each return to the upper end position, it can be detected that the remaining amount in each of the reagent containers 200, 200, . . . and the reagent container 201 is the predetermined amount or less. When the ends of the fluid channels 210, 210, . . . and the fluid channel 211 located on the side of the reagent containers 200, 200, . . . and the reagent container 201 are arranged in such a manner that reagents are aspirated from the bottom surfaces of the reagent containers 200, 200, . . . and the reagent container 201, the reagents can be aspirated until the reagent containers 200, 200, . . . and the reagent container 201 become empty and thereby the reagents in the reagent containers 200, 200, . . . and the reagent container 201 can be inhibited from being wasted. On the other hand, when the ends of the fluid channels 210, 210, . . . and the fluid channel 211 located on the side of the reagent containers 200, 200, . . . and the reagent container 201 are arranged in such a manner that the reagents are aspirated from a predetermined distance above the bottom surfaces of the reagent containers 200, 200, . . . and the reagent container 201, entry of air bubbles into the reagent storage sections 250, 250, . . . and the reagent storage section 251 can be inhibited.

In the sample analyzer 1 according to Embodiment 1, even when the message such as "Please replace the reagent container" or "No reagent" is outputted to the image display unit 12a of the control unit 12, the reagent storage sections 250, 250, . . . and the reagent storage section 251 still contain reagents stored therein. Therefore, it is not necessary to immediately suspend the measurement process in the measurement unit 5 (5a, 5b) at the time when the message such as "Please replace the reagent container" or "No reagent" is outputted to the image display unit 12a of the control unit 12 and the reagents are transferred continuously from the reagent storage sections 250, 250, . . . and the reagent storage section 251 to the measurement unit 5 (5a, 5b). Examples of the method for detecting that the remaining amount in each of the reagent storage sections 250, 250, . . . and the reagent storage section 251 is the predetermined amount or less include a method in which an amount obtained by multiplying the amount of the reagent required for a single measurement of a sample in the measurement unit 5 (5a, 5b) by the number of times of measurement is subtracted from the remaining amount in each of the reagent storage sections 250, 250, . . . and the reagent storage section 251 at the time when the replacement message is outputted, and the result of subtraction is compared with the reagent storage remaining amount stored in the remaining amount determination information storage section 1231. In this connection, the remaining amount in each of the reagent storage sections 250, 250, . . . and the reagent storage section 251 at the time when the replacement message is outputted is calculated from the position of the float boards of each of the float switches 260, 260, . . . and the float switch 261.

Furthermore, the method for detecting that the remaining amount in each of the reagent storage sections 250, 250, . . . and the reagent storage section 251 is the predetermined amount or less can be a method for detecting it according to the number of times the measurement can be carried out without replacing the reagent containers. In this case, the number of times the measurement can be carried out without replacing the reagent containers at the time when the replacement message is outputted is stored in the remaining amount determination information storage section 1231, and the number of times of measurement is counted each time the measurement is carried out after the time when the message such as "Please replace the reagent container" is outputted to the image display unit 12*a* of the control unit 12. When the counted number of times of measurement reaches the number of times the measurement can be carried out, which is stored in the remaining amount determination information storage section 1231, it can be detected that the remaining amount in each of the reagent storage sections 250, 250, . . . and the reagent storage section 251 is the predetermined amount or less and thereby a message for prompting to suspend sample measurement, such as "Please replace the reagent container (unmeasurable)" is outputted to the image display unit 12*a* of the control unit 12. Also, it can be detected that the remaining amount in each of the reagent storage sections 250, 250, . . . and the reagent storage section 251 is the predetermined amount or less when the number of times the measurement can be carried out, which is stored, is decremented by one each time the sample is measured, and becomes zero.

The amount of the reagent, which also serves as a diluent, a lavage fluid, and a sheath fluid, contained in the reagent container 201 is larger than those contained in the other reagent containers 200, 200, . . . . Therefore, the amount of the reagent stored in the reagent storage section 251 also is larger than those contained in the other reagent storage sections 250, 250, . . . and so is the amount of the reagent to be used for a single measurement. Accordingly, there is a possibility that the remaining amount in the reagent container 201 may not be detected accurately by the above-mentioned method of counting the number of times of measurement.

Therefore, for example, air bubble sensors 280, 280, . . . may also be provided inside the measurement unit 5 (5*a*, 5*b*), and thereby it can be detected that the remaining amount in each of the reagent storage sections 250, 250, . . . and the reagent storage section 251 is the predetermined amount or less at the time when detecting generation of air bubbles. Then the message such as "Please replace the reagent container (unmeasurable)" is outputted to the image display unit 12*a* of the control unit 12.

Furthermore, the reagent storage section 251 may be provided with the float switch 261 having two float boards (one in the upper part and the other in the lower part), and the float board in the upper part may detect that the remaining amount in the reagent container 201 is the predetermined amount or less while the float board in the lower part may detect that the remaining amount in the reagent storage section 251 is the predetermined amount or less. Thus, with respect to the reagent storage section 251 in which a larger amount of reagent is used for a single measurement, it can be detected with high accuracy that the remaining amount is the predetermined amount or less.

In the case where the counted number of times of measurement reaches the stored number of times measurement can be carried out or in the case where it can be detected that the remaining amount in each of the reagent storage sections 250, 250, . . . and the reagent storage section 251 is the predetermined amount or less, when the fluid level of the reagent can no longer be detected by the float board in the lower part, it is preferable to suspend transfer of the reagents to the measurement unit 5 (5*a*, 5*b*). Since an amount of reagent required for measurement does not remain, transfer itself is suspended and thereby there is no possibility that reagents are wastefully mixed with samples to prepare measurement samples that would not be measured. Thus, valuable samples can be prevented from being wasted.

Preferably, the number of counts (the number of times measurement can be carried out) to be stored in the remaining amount determination information storage section 1231 of the control unit 12 is at least the maximum number of samples that the sample transporting unit 3 can accommodate. In this case, transfer of the reagents from the reagent containers 200, 200, . . . and the reagent container 201 to the reagent storage sections 250, 250, . . . and the reagent storage section 251 is controlled in such a manner that the remaining amount in each of the reagent storage sections 250, 250, . . . and the reagent storage section 251 is larger than the amount that allows samples of the stored number of counts to be measured. In the case where the number of counts is at least the maximum number of samples that can be accommodated by the sample transporting unit 3 as samples to be measured, for example, 50, when it is detected that the remaining amount in each of the reagent containers 200, 200, . . . and the reagent container 201 is the predetermined amount or less and thereby the message such as "Please replace the reagent container" is outputted to the image display unit 12*a* of the control unit 12, with respect to the samples that have been accommodated by the sample transporting unit 3 as samples to be measured, measurement can be completed using the reagents stored in the reagent storage sections 250, 250, . . . and the reagent storage section 251. Therefore, with respect to the samples that have been accommodated by the sample transporting unit 3, it is possible to prevent measurement from being suspended due to insufficiency of the reagents. This makes it easier for the user of the sample analyzer 1 to leave the sample analyzer 1 unattended after the samples are accommodated by the sample transporting unit 3 as the samples to be measured, and to perform other work.

Figure 6:
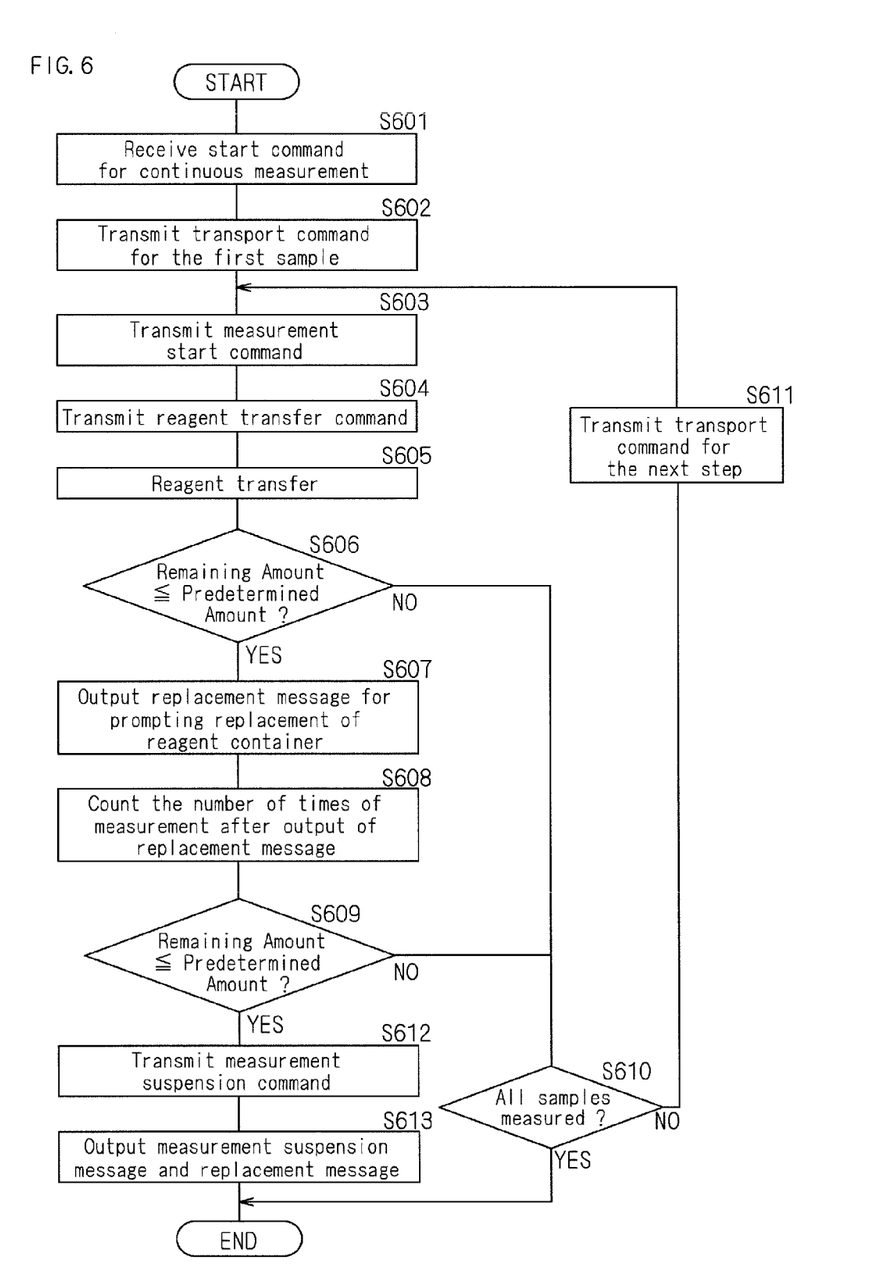
FIG. 6 is a flow chart showing the control procedure for measurement process in a CPU of the control unit according to Embodiment 1 of the present invention.

FIG. 6 is a flow chart showing the control procedure for measurement process in the CPU 121 of the control unit 12 according to Embodiment 1 of the present invention. In FIG. 6, the CPU 121 of the control unit 12 receives a start command for continuous sample measurement (Step S601). The start command is received, for example, through the input unit 12*b*. The start command thus received is transmitted to the control section 500 of the measurement unit 5 (5*a*, 5*b*). The control section 500 that has received the start command controls operation of the air pressure source unit 252 and the valves 275, 275, . . . to fill the reagent storage sections 250, 250, . . . and the reagent storage section 251 with reagents.

The CPU 121 transmits a transport command for the first sample to be measured to the control section 300 of the sample transporting unit 3 (Step S602). The control section 300 of the sample transporting unit 3 that has received the transport command allows the sample container T containing the sample to be measured to be transported to the aspiration section.

The CPU 121 transmits a measurement start command to the control section 500 of the measurement unit 5 (5*a*, 5*b*) (Step S603). The CPU 121 transmits a transfer command for a reagent to be required according to the measurement item, to the control section 500 of the measurement unit 5 (5*a*, 5*b*) (Step S604). The control section 500 that has received the transfer command controls operation of the air pressure source unit 252 and the valves 275, 275, . . . to transfer the reagents from the reagent storage sections 250, 250, . . . and the reagent storage section 251 to the measurement unit 5 (5*a*, 5*b*). The measurement unit 5 (5*a*, 5*b*) to which the reagents have been transferred mixes samples to be measured with the reagents to prepare measurement samples according to the command of the control section 500, then measures a predetermined property value, for example, the blood count.

The CPU 121 transfers reagents from the reagent containers 200, 200, . . . and the reagent container 201 to the reagent storage sections 250, 250, . . . and the reagent storage section 251 (Step S605) and determines whether the remaining amount in each of the reagent containers 200, 200, . . . and the reagent container 201 is the predetermined amount or less based on whether the float boards of the float switches 260, 260, . . . and the float switch 261 each return to the upper end position (Step S606). When the CPU 121 determines that the remaining amount is the predetermined amount or less (Step S606: YES), the CPU 121 outputs the message (the replacement message) for prompting replacement of the reagent containers 200, 200, . . . and the reagent container 201 to the image display unit 12*a* of the control unit 12 (Step S607). Then the CPU 121 counts the number of samples measured after the replacement message is outputted, i.e. the number of times of measurement (Step S608). The replacement message outputted at Step S607 contains the number of times measurement can be carried out without replacing the reagent containers, which is stored in the remaining amount determination information storage section 1231. Furthermore, the CPU 121 controls the image display unit 12*a* in such a manner that the number of times measurement can be carried out, which is contained in the replacement message, is decremented by one each time a sample is measured (that is, each time the process returns to Step S603). This allows the user to recognize the number of samples that can be measured in real time.

The CPU 121 determines whether the remaining amount in each of the reagent storage sections 250, 250, . . . and the reagent storage section 251 is the predetermined amount, which is stored in the remaining amount determination information storage section 1231, or less (Step S609). That is, the CPU 121 determines whether the counted number of times of measurement reaches the number of times measurement can be carried out without replacing the reagent containers, which is stored in the remaining amount determination information storage section 1231. When the CPU 121 determines that the counted number of times of measurement reaches the stored number of times, that is, when the CPU 121 determines that the remaining amount in each of the reagent storage sections 250, 250, . . . and the reagent storage section 251 is the predetermined amount or less (Step S609: YES), the CPU 121 transmits a measurement suspension command to the control section 500 of the measurement unit 5 (5*a*, 5*b*) (Step S612) and outputs the measurement suspension message for prompting suspension of measurement and the replacement message for prompting replacement of the reagent containers 200, 200, . . . and the reagent container 201 to the image display unit 12*a* of the control unit 12 (Step S613).

When the CPU 121 determines that the remaining amount is larger than the predetermined amount (Step S606: NO and Step S609: NO), the CPU 121 determines whether measurement of all the samples has been completed (Step S610). When the CPU 121 determines that samples that have not been measured still exist (Step S610: NO), the CPU 121 transmits a transport command for the next sample to be measured to the control section 300 of the sample transporting unit 3 (Step S611) and returns the process to Step S603 to repeat the processes described above. When the CPU 121 determines that the measurement of all the samples has been completed (Step S610: YES), the CPU 121 ends the process.

As described above, since the sample analyzer 1 according to Embodiment 1 comprises the reagent storage sections 250, 250, . . . and the reagent storage section 251, it is not necessary to connect a plurality of reagent containers 200, 200, . . . and reagent containers 201 containing the same types of reagents, respectively. In Embodiment 1, even when the reagent containers 200, 200, . . . and the reagent container 201 become empty, sample measurement can be continued using the reagents stored in the reagent storage sections 250, 250, . . . and the reagent storage section 251 without interruption. Furthermore, since the message for prompting replacement of the reagent containers 200, 200, . . . and the reagent container 201 is outputted at the time when the reagent containers 200, 200, . . . and the reagent container 201 become empty, the user can replace the reagent containers to replenish reagents without interrupting measurement.

Embodiment 2

Figure 7:
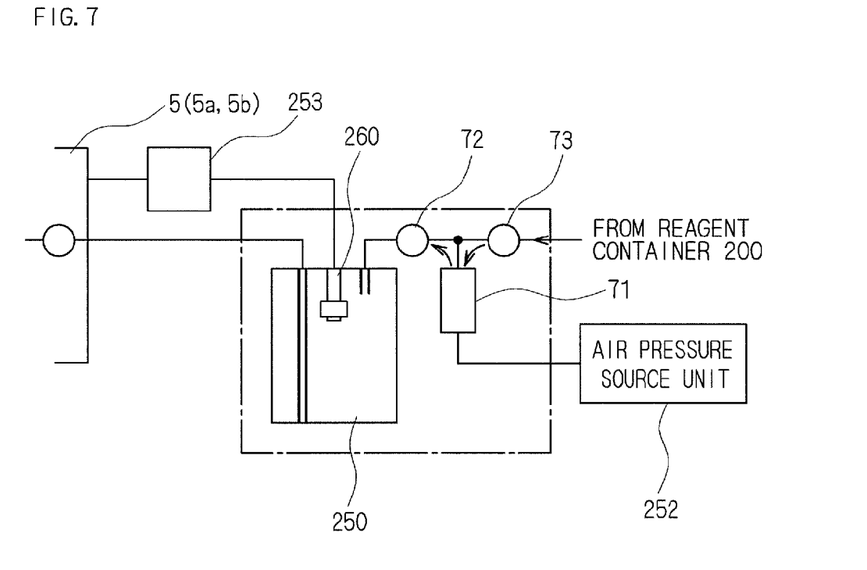
FIG. 7 is a schematic view showing the outline configuration for transferring a reagent in a reagent container setting section of a sample analyzer according to Embodiment 2 of the present invention.

The configuration of a sample analyzer according to Embodiment 2 of the present invention is similar to that of Embodiment 1. Therefore the same numbers and symbols are used and detailed descriptions are not repeated. Embodiment 2 is different from Embodiment 1 in that a pump is used for transferring a reagent from a reagent container 200 to a reagent storage section 250.

FIG. 7 is a schematic view showing the outline configuration for transferring a reagent in the reagent container setting section 2 of the sample analyzer 1 according to Embodiment 2 of the present invention. As shown in FIG. 7, the reagent storage section 250 is provided between the reagent container 200 and the measurement unit 5 (5*a*, 5*b*) and a diaphragm pump 71 for transferring the reagent from the reagent container 200 is provided. When the reagent is transferred from the reagent container 200 to the reagent storage section 250, first a valve 73 is opened and the air pressure source unit 252 applies negative pressure to the diaphragm pump 71 and thereby the reagent is transferred from the reagent container 200 to the diaphragm pump 71. Then the valve 73 is closed and a valve 72 is opened, so that the air pressure source unit 252 applies positive pressure to the diaphragm pump 71 and thereby the reagent is transferred from the diaphragm pump 71 to the reagent storage section 250.

Next, as in the case of Embodiment 1, when samples are measured, the air pressure source unit 252 applies positive pressure and negative pressure to the diaphragm pump 290 (see FIG. 8) provided for the measurement unit 5 (5*a*, 5*b*). Accordingly, the reagent stored in the reagent storage section 250 is transferred to the measurement unit 5 (5*a*, 5*b*) and the float board of the float switch 260 descends from the position (upper end position) at which the float board was located when the reagent was filled.

The diaphragm pump 71 is driven each time measurement of one sample is completed and thereby the reagent is transferred from the reagent container 200 to the reagent storage section 250. This allows the float board of the float switch 260 to return to the position (upper end position) at which the float board was located before descending, that is, the position at which the float board was located when the reagent was filled.

When the reagent containers 200, 200, . . . and the reagent container 201 become empty (i.e. the remaining amount is the predetermined amount or less), the detection circuit 253 receives a signal from the float switch 260 to be described later and transmits a predetermined signal to the measurement unit 5 (5a, 5b).

Figure 8:
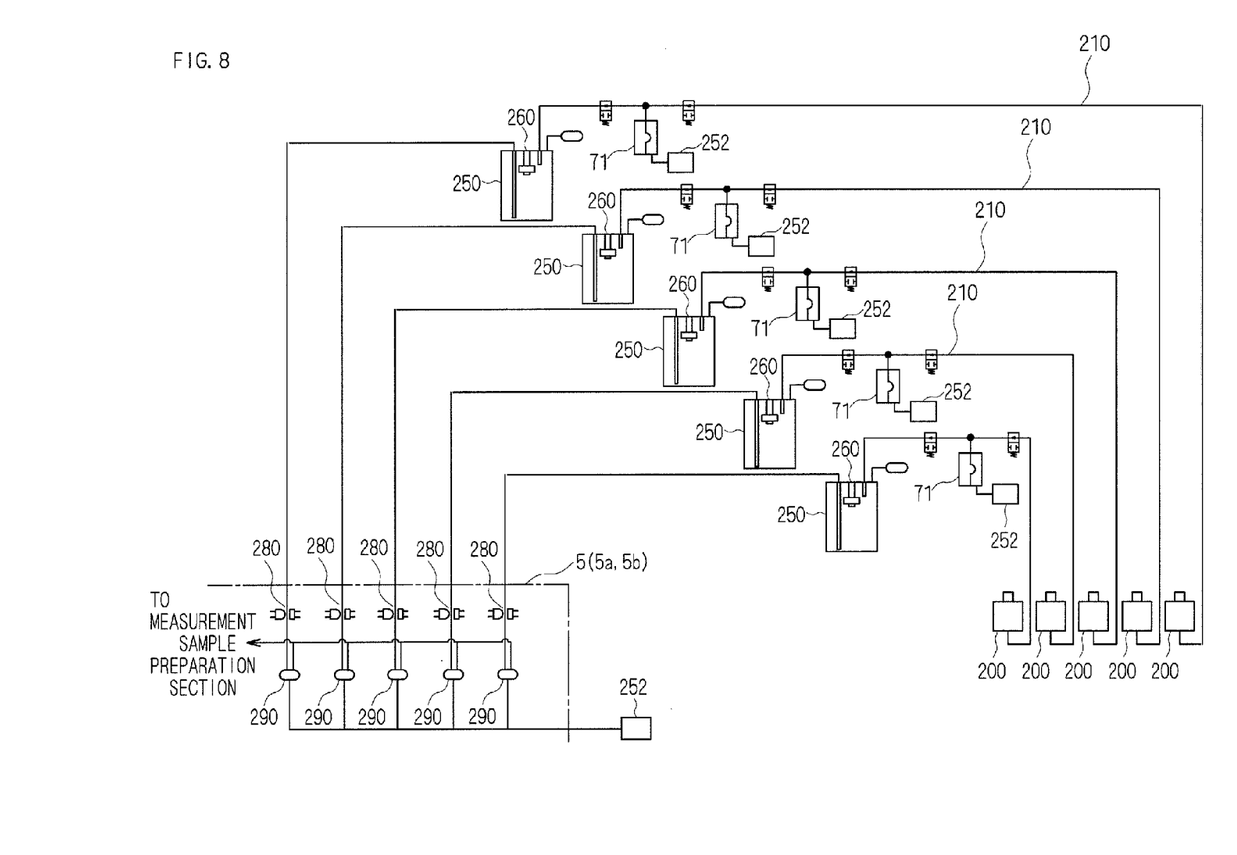
FIG. 8 is a circuit diagram showing the configuration of a reagent supply circuit of the sample analyzer according to Embodiment 2 of the present invention.

FIG. 8 is a circuit diagram showing the configuration of a reagent supply circuit of the sample analyzer 1 according to Embodiment 2 of the present invention. Reagents are supplied from the reagent containers 200, 200, . . . to the measurement unit 5 (5a, 5b) through the fluid channels 210, 210, . . . . Chambers are arranged as the reagent storage sections 250, 250, . . . midway through the fluid channels 210, 210, . . . , respectively.

During the start-up of the sample analyzer 1 or replacement of the reagent containers 200, 200, . . . , the diaphragm pumps 71, 71, . . . are driven to transfer the reagents from the reagent containers 200, 200, . . . to the reagent storage sections 250, 250, . . . .

In the state where the reagent storage sections 250, 250, . . . as well as the fluid channels 210, 210, . . . are filled with the reagents, the diaphragm pumps 290, 290, . . . provided inside the measurement unit 5 (5a, 5b) are driven, so that the reagents are transferred from the reagent storage sections 250, 250, . . . to the measurement unit 5 (5a, 5b).

The float switches 260, 260, . . . are provided inside the reagent storage sections 250, 250, . . . . When the reagents are transferred from the reagent storage sections 250, 250, . . . to the measurement unit 5 (5a, 5b) and thereby the float boards of the float switches 260, 260, . . . descend, as in the case during the start-up of the sample analyzer 1 or replacement of the reagent containers 200, 200, . . . , the diaphragm pumps 71, 71, . . . are driven to transfer reagents from the reagent containers 200, 200, . . . to the reagent storage sections 250, 250, . . . and transfer of the reagents is suspended at the time when the float boards of the float switches 260, 260, . . . each return to the position (upper end position) at which they were located before descending.

On the other hand, in the case where the reagents are transferred from the reagent containers 200, 200, . . . to the reagent storage sections 250, 250, . . . , when the float boards of the float switches 260, 260, . . . do not return to the upper end position even after the diaphragm pumps 71, 71, . . . are driven a predetermined number of times, it can be detected that the remaining amount in each of the reagent containers 200, 200, . . . is the predetermined amount or less and the message such as "Please replace the reagent container" is outputted to the image display unit 12a of the control unit 12.

Even at the time when the message such as "Please replace the reagent container" is outputted to the image display unit 12a of the control unit 12, reagents are still stored in the reagent storage sections 250, 250, . . . . Therefore, it is not necessary to immediately suspend the measurement process in the measurement unit 5 (5a, 5b) at the time when the message such as "Please replace the reagent container" is outputted to the image display unit 12a of the control unit 12.

Since Embodiment 1 and Embodiment 2 are different from each other only in the method for transferring reagents and are not so much different from each other in the control procedure for the measurement process in the CPU 121, the description of the control procedure for the measurement process in the CPU 121 is not repeated.

As described above, since the sample analyzer 1 according to Embodiment 2 comprises the reagent storage sections 250, 250, . . . , it is not necessary to connect a plurality of reagent containers 200, 200, . . . containing the same type of reagent. In Embodiment 2, even when the reagent containers 200, 200, . . . become empty, samples measurement can be continued using the reagents stored in the reagent storage sections 250, 250, . . . without interruption. Furthermore, since the message for prompting replacement of the reagent containers 200, 200, . . . is outputted at the time when the reagent containers 200, 200, . . . become empty, the user can replace the reagent containers to replenish reagents without interrupting measurement.

Embodiment 3

Figure 9:
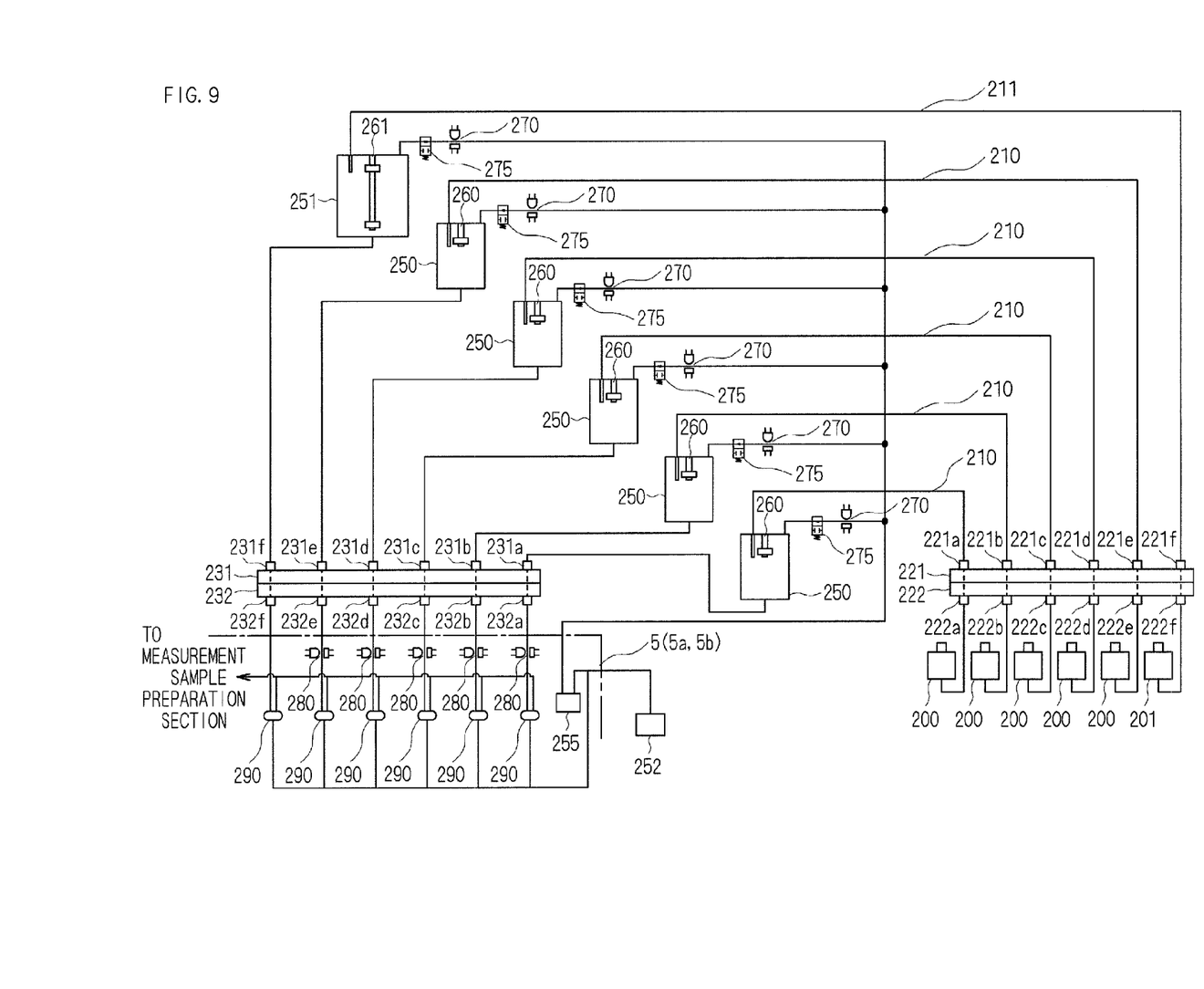
FIG. 9 is a circuit diagram showing the configuration of a reagent supply circuit of a sample analyzer according to Embodiment 3 of the present invention.

The configuration of a sample analyzer according to Embodiment 3 of the present invention is similar to that of Embodiment 1. Therefore the same numbers and symbols are used and detailed descriptions are not repeated. Embodiment 3 is different from Embodiment 1 in that a fluid connector (a second fluid connector), a fluid connector (a first fluid connector), a fluid connector (a third fluid connector), and a fluid connector (a fourth fluid connector) are provided in the fluid channels 210, 210, . . . and the fluid channel 211.

FIG. 9 is a circuit diagram showing the configuration of a reagent supply circuit of the sample analyzer 1 according to Embodiment 3 of the present invention. In the example shown in FIG. 9, a fluid connector (a second fluid connector) 221 and a fluid connector (a first fluid connector) 222 are provided between the reagent containers 200, 200, . . . and the reagent container 201 and the reagent storage sections 250, 250, . . . and the reagent storage section 251 in the fluid channels 210, 210, . . . and the fluid channel 211. The fluid connector 221 has ports 221a, 221b, . . . and 221f, while the fluid connector 222 has ports 222a, 222b, . . . and 222f. The fluid connector 221 and the fluid connector 222 are detachably connected to each other. The fluid connector 221 and the fluid connector 222 are configured in such a manner that when they are connected to each other, the port 221a, the port 221b, . . . and the port 221f communicate with the port 222a, the port 222b, . . . and the port 222f, respectively.

Furthermore, a fluid connector (a third fluid connector) 231 and a fluid connector (a fourth fluid connector) 232 are provided between the reagent storage sections 250, 250, . . . and the reagent storage section 251 and the diaphragm pumps 290, 290, . . . . The fluid connector 231 has ports 231a, 231b, . . . , and 231f, while the fluid connector 232 has ports 232a, 232b, . . . , and 232f. The fluid connector 231 and the fluid connector 232 are detachably connected to each other. The fluid connector 231 and the fluid connector 232 are configured in such a manner that when they are connected to each other, the port 231a, the port 231b, . . . and the port 231f communicate with the port 232a, the port 232b, . . . and the port 232f, respectively.

In the above-mentioned configuration, when failures occur in fluid components in a fluid circuit such as the float switches 260, 260, . . . , the float switch 261, the air bubble sensors 270, 270, . . . , and the valves 275, 275, . . . , the connection between the fluid connector 221 and the fluid connector 222 as well as the connection between the fluid connector 231 and the fluid connector 232 each are disconnected to separate the fluid components from the fluid circuit interposed between the fluid connector (the second fluid connector) 221 and the fluid connector (the third fluid connector) 231, and the fluid connector (the first fluid connector) 222 and the fluid connector (the fourth fluid connector) 232 can be directly connected to each other. The fluid connector 222 and the fluid connector 232 are configured in such a manner that when they are connected to each other, the port 222a, the port 222b, . . . , and the port 222f communicate with the port 232a, the port 232b, . . . , and the port 232f, respectively. This allows the fluid components to be bypassed and the measurement unit 5 (5a, 5b) to directly aspirate reagents from the reagent containers 200, 200, . . . and the reagent container 201. Therefore, the sample analyzer 1 can carry out measurement continuously. In this connection, the fluid connectors to be used can be those disclosed in, for example, JP 2531074 Y.

As described above, the sample analyzer 1 according to Embodiment 3 comprises, in the fluid channels 210, 210, . . . and the fluid channel 211, the fluid connector 221 and the fluid connector 222 between the reagent containers 200, 200, . . . and the reagent container 201 and the reagent storage sections 250, 250, . . . and the reagent storage section 251 as well as the fluid connector 231 and the fluid connector 232 between the reagent storage sections 250, 250, . . . and the reagent storage section 251 and the diaphragm pumps 290, 290, . . . . Therefore, even when failures occur in the fluid components, the fluid connector 222 and the fluid connector 232 can be directly connected to each other and thereby the measurement unit 5 (5a, 5b) can directly aspirate reagents from the reagent containers 200, 200, . . . and the reagent container 201. This allows the sample analyzer 1 to carry out measurement continuously.

Further, the present invention is not limited to Embodiments 1, 2, and 3 described above and, for example, various modification and substitution can be made within the spirit of the present invention. For instance, a weight sensor that directly measures the weight of the reagent container itself or a fluid level sensor that detects the height of the fluid level in the reagent container may be used as a sensor for detecting that the remaining amount in a reagent container is a predetermined amount or less. Furthermore, for example, a weight sensor or a fluid level sensor may also be used for detecting that the remaining amount in a reagent storage section is a predetermined amount or less.

In Embodiments 1, 2, and 3 described above, diaphragm pumps or an air pressure source unit used for transferring reagents from the reagent containers to the reagent storage sections are different from those used for transferring reagents from the reagent storage sections to measurement units. However, one diaphragm pump may be used for both purposes. This also makes it possible to reduce the capacity of a reagent container setting section.

Furthermore, in Embodiments 1, 2, and 3 described above, only one reagent container containing the same type of reagent is connected but a plurality of reagent containers containing the same type of reagent may be connected.

Moreover, in Embodiments 1, 2, and 3 described above, the CPU 121 of the control unit 12, the control section 300 of the sample transporting unit 3, and the control section 500 of the measurement unit 5 are provided as the control sections for controlling operation of respective sections of the sample analyzer 1. However, it can be configured without being distributed in such a manner that one control section controls operation collectively.

What is claimed is:
1. A sample analyzer comprising:
    a reagent container setting section configured to set a reagent container;
    a reagent storage section connected to the reagent container through a first fluid channel;
    a measurement section connected to the reagent storage section through a second fluid channel, wherein the measurement section comprising a measurement sample preparation section that prepares a measurement sample from a sample and reagent transferred through the second fluid channel from the reagent container;
    an air pressure source operable to apply a negative pressure to the reagent storage section through the second fluid channel via a diaphragm pump which is driven by the air pressure source; and
    a controller programmed to: control through switching a valve on a third fluid channel which is disposed between the air pressure source and the reagent storage section, such that:
    (1) when the valve is switched open, direct the air pressure source to apply the negative pressure to the third fluid channel, to transfer reagent through the first fluid channel from the reagent container to the reagent storage section; and
    (2) when the valve is switched closed, operate the diaphragm pump to transfer the reagent stored in the reagent storage section to the measurement section through applying the negative pressure in the second fluid channel.
2. The sample analyzer according to claim 1, further comprising a reagent container remaining amount detector configured to detect whether a remaining amount in the reagent container is at or less than a predetermined amount; and
    a display configured to display output for promoting replacement of the reagent container when the reagent container remaining amount detector detects the remaining amount in the reagent container is less than the predetermined amount.
3. The sample analyzer according to claim 1, wherein when a reagent container remaining amount detector detects that a remaining amount in the reagent container is at or less than a predetermined amount, the reagent is transferred from the reagent container to the reagent storage section.
4. The sample analyzer according to claim 1, wherein
    the diaphragm pump quantitates the reagent transferred to the measurement section and transfers the quantitated reagent to the measurement sample preparation section.
5. The sample analyzer according to claim 1, further comprising a plurality of the first fluid channels, the reagent storage sections and the second fluid channels corresponding to reagent containers for a plurality of types of reagent,
    wherein the air pressure source applies the negative pressure to each of the plurality of the second fluid channels.

* * * * *